(12) United States Patent
Grychowski et al.

(10) Patent No.: US 7,201,164 B2
(45) Date of Patent: Apr. 10, 2007

(54) AEROSOL MEDICATION DELIVERY APPARATUS WITH NARROW ORIFICE

(75) Inventors: Jerry R. Grychowski, Lake Zurich, IL (US); Martin P. Foley, London (CA)

(73) Assignee: Trudell Medical International, London, Ontario (CA)

( * ) Notice: Subject to any disclaimer, the term of this patent is extended or adjusted under 35 U.S.C. 154(b) by 37 days.

(21) Appl. No.: 10/979,743

(22) Filed: Nov. 2, 2004

(65) Prior Publication Data
US 2005/0126561 A1 Jun. 16, 2005

Related U.S. Application Data

(63) Continuation of application No. PCT/US03/12121, filed on May 2, 2003.

(60) Provisional application No. 60/377,528, filed on May 3, 2002.

(51) Int. Cl.
*A61M 11/00* (2006.01)

(52) U.S. Cl. .......................... 128/200.23; 128/200.22; 128/203.12

(58) Field of Classification Search ........... 128/200.23, 128/200.22, 203.12
See application file for complete search history.

(56) References Cited

U.S. PATENT DOCUMENTS

| | | | |
|---|---|---|---|
| 4,470,412 A | 9/1984 | Nowacki et al. | |
| 5,669,376 A | 9/1997 | Sioutas | |
| 5,746,197 A | 5/1998 | Williams | |
| 5,881,718 A | 3/1999 | Mortensen et al. | |
| 5,899,201 A | 5/1999 | Schultz et al. | |
| 5,988,160 A * | 11/1999 | Foley et al. | 128/200.22 |
| 6,070,573 A | 6/2000 | Howe et al. | |
| 6,085,742 A | 7/2000 | Wachter et al. | |
| 6,095,141 A | 8/2000 | Armer et al. | |
| 6,293,279 B1 | 9/2001 | Schmidt et al. | |
| 6,345,617 B1 | 2/2002 | Engelbreth et al. | |

FOREIGN PATENT DOCUMENTS

WO WO 03/092777 A1 11/2003

OTHER PUBLICATIONS

International Search Report, PCT/US03/12121, mailed Oct. 6, 2003, 1 page.
Photos of valve and spacer device available from Astra Aktiekolag, Sweden, prior to May 3, 2002, 4 pages.

* cited by examiner

*Primary Examiner*—Henry Bennett
(74) *Attorney, Agent, or Firm*—Brinks Hofer Gilson & Lione

(57) ABSTRACT

An aerosol medication delivery apparatus includes a holding chamber having an input end and an output end and defining an interior space. The output end comprises an orifice having a cross-sectional area of less than about 60 mm$^2$. In one preferred embodiment, the orifice has a circular cross-section. Preferably, the orifice has a diameter of between about 2.0 mm and about 7.50 mm. In one preferred embodiment, an inhalation and exhalation valve is located at the output end. A method of using the holding chamber is also provided.

33 Claims, 5 Drawing Sheets

AEROSOL MEDICATION DELIVERY APPARATUS WITH NARROW ORIFICE

This application is a continuation of International Application PCT/US03/12121, with an international filing date of May 2, 2003, which claims the benefit of U.S. Provisional Application No. 60/377,528, filed May 3, 2002, the entire disclosures of which are hereby incorporated herein by reference.

BACKGROUND

The present invention relates to an aerosol delivery apparatus, and in particular, to an aerosol medication delivery apparatus having a narrow orifice.

Aerosol medication delivery systems are used, in general, to administer medication in aerosol form to the lungs of a user. For example, some systems use a pressurized metered-dose inhaler (pMDI), which typically includes a container in which the medication particles are stored under pressure, and an actuator used to dispense the medication from the container. In other systems, a holding chamber is connected to one of the container or actuator, as shown for example in U.S. Pat. No. 6,293,279, assigned to Trudell Medical International, and which is hereby incorporated herein by reference. The holding chamber reduces the need for the user to coordinate activation of the pMDI canister with inhalation, helps reduce the delivery of nonrespirable medication particles from the canister, and helps reduce the impaction of medication particles in the user's oropharnyx and upper airway. In some configurations, shown for example in the U.S. Pat. Nos. 6,293,279 and 5,881,718, the apparatus can be provided with one or both of an inhalation and exhalation valve(s) at an output end of the chamber. The output end is typically configured with a mouthpiece, which is received in the mouth of the user, or with a mask, which is placed over the mouth and nose of the user.

Users of the aforementioned devices often suffer from various bronchial ailments that can reduce lung capacity and output, which problems can be exacerbated with young children and domestic cats and dogs. Many of these devices, however, are not especially suited for users with low tidal volumes, such as neonatals. In particular, such devices typically have an orifice at the output end of the holding chamber that is greater than 78 mm$^2$. Such relatively large openings may not produce the sweeping force necessary to draw aerosol out of a chamber with low tidal volumes, especially when the device is configured with inhalation/exhalation valves. As used herein, the word "user" includes humans and animals, including domestic cats and dogs.

SUMMARY

By way of introduction, various preferred embodiments of an aerosol medication delivery apparatus include a holding chamber having an input end and an output end and defining a chamber housing having an interior space. The length of the chamber housing as measured from the input end to the output end is at least 70 mm and the diameter of the holding chamber is at least 20 mm. In one preferred embodiment, the chamber housing has a length of 120 mm and the diameter of the holding chamber is 40 mm. The output end comprises an orifice having a cross-sectional area of less than about 60 mm$^2$. In one preferred embodiment, the orifice has a circular cross-section. Preferably, the orifice has a diameter of between about 2.0 mm and about 7.5 mm.

In one aspect, one preferred embodiment of the apparatus includes an inhalation and exhalation valve at the output end. In other aspects, methods of using the holding chamber are provided.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

DETAILED DESCRIPTION OF THE PRESENTLY PREFERRED EMBODIMENTS

Figure 1:
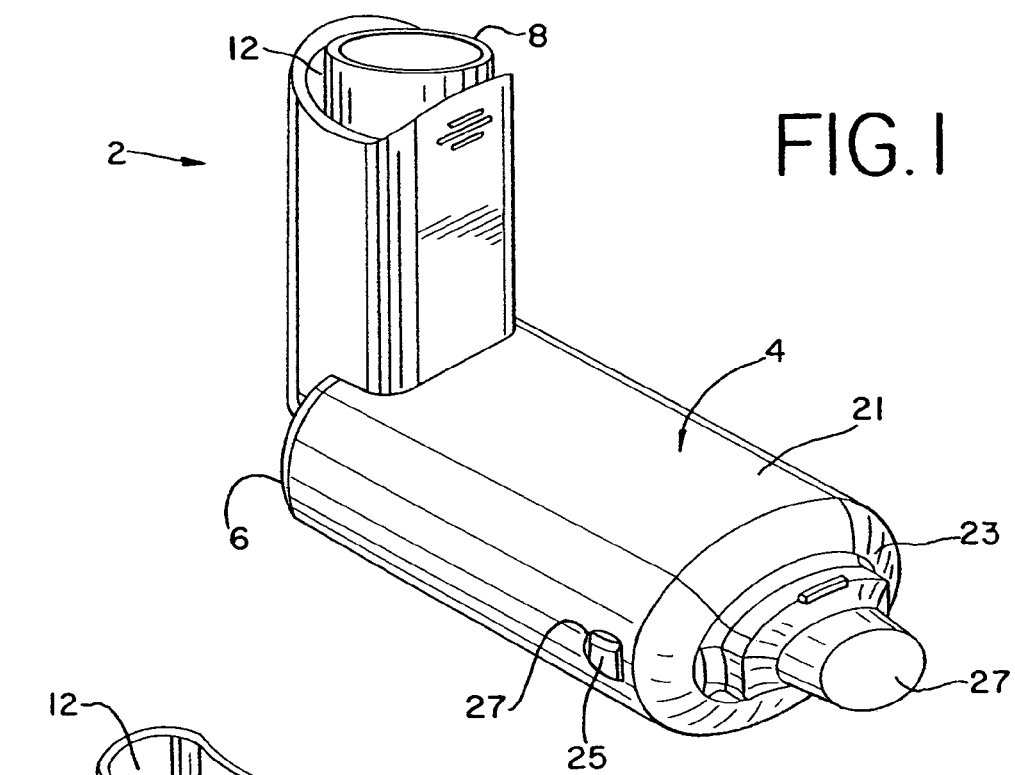
FIG. 1 is a perspective view of an aerosol medication delivery system.
Figure 2:
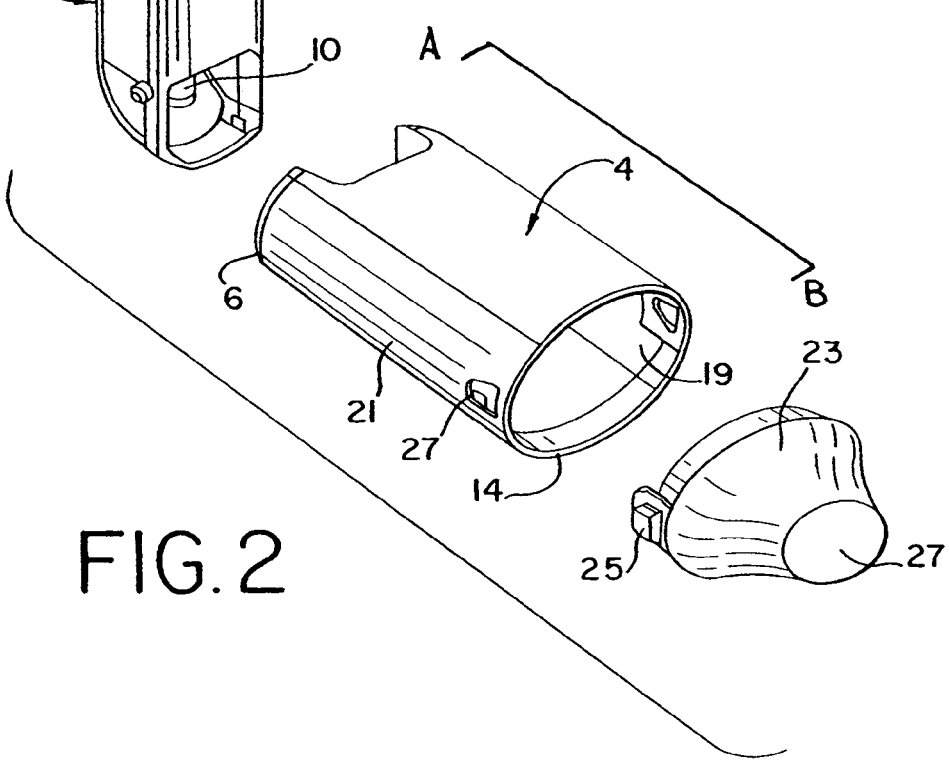
FIG. 2 is an exploded perspective view of the aerosol medication delivery system shown in FIG. 1.

Referring to FIGS. 1 and 2, one preferred embodiment of an aerosol medication delivery system includes a pMDI canister holding portion 2, or dispenser, coupled to a chamber housing 4, otherwise referred to as a holding chamber, at an input end 6 thereof. A medication container 8, for example a pMDI canister is disposed in a cavity 12 formed in the dispenser, with a stem of the canister being inserted into a well 10 formed in the bottom of the dispenser. Preferably, the dispenser 2 is pivotally connected to the chamber housing 4 so that the dispenser 2 can be pivoted and translated for storage inside the chamber housing when the device is not in use. The term "medication" or "medicament" and variations thereof as used herein means any substance used in therapy.

Figure 3:
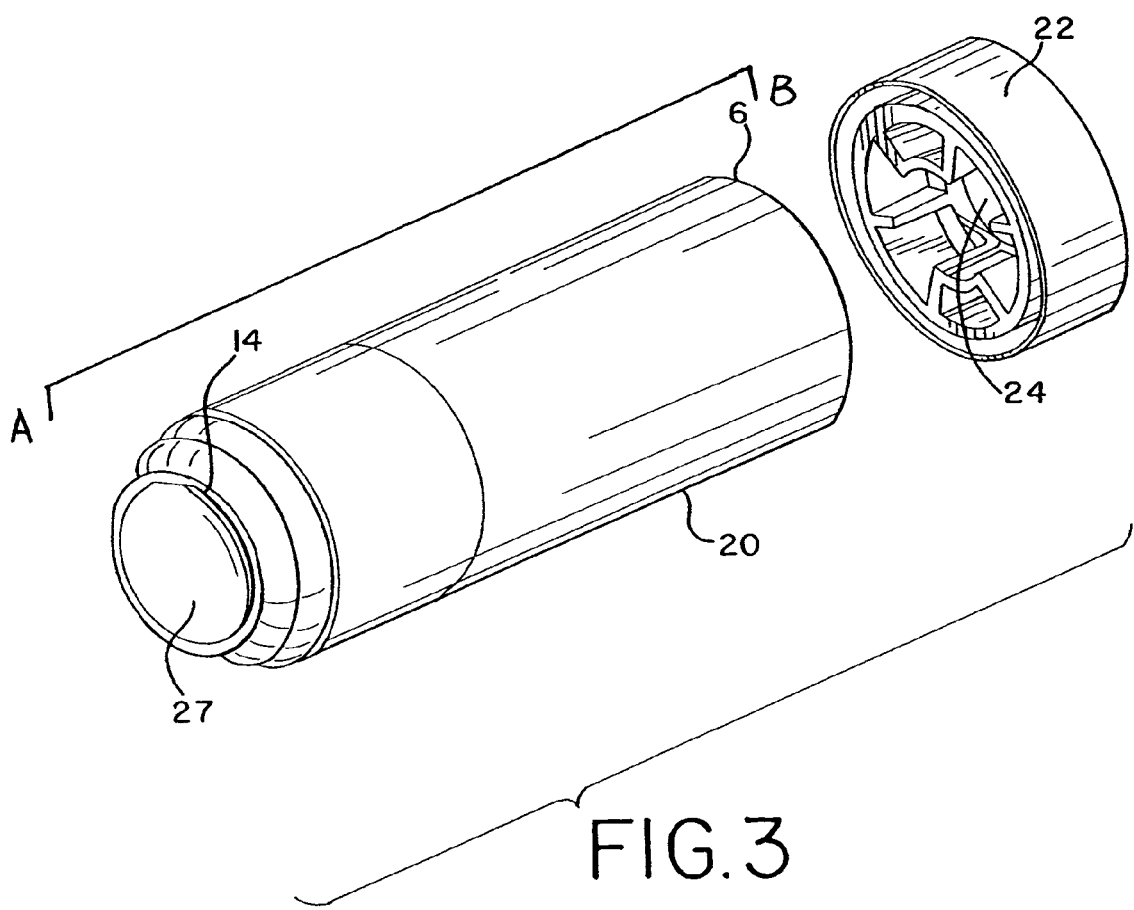
FIG. 3 is an exploded perspective view of an alternative embodiment of a holding chamber.
Figure 4:
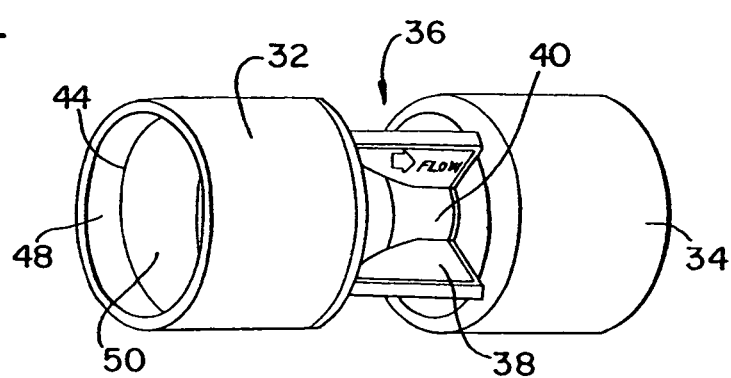
FIG. 4 is a perspective view of one preferred embodiment of an adapter.
Figure 5:
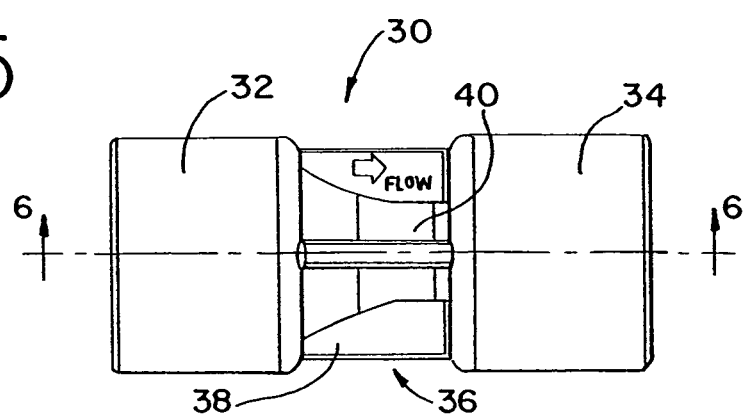
FIG. 5 is a side view of the adapter shown in FIG. 4.

In an alternative embodiment shown in FIG. 3, the apparatus does not include an integrated dispenser secured to the holding portion 20, but rather includes a backpiece 22 at the input end thereof. The backpiece 22 is preferably made of an elastomeric material and includes an opening 24 shaped to receive a mouthpiece portion of a separate pMDI dispenser. Various configurations of chamber housings and dispensers are shown in U.S. Pat. Nos. 6,293,279, 5,012,803, and 5,012,804, the entire disclosures of which are hereby incorporated herein by reference. It should be understood that a holding chamber can also be used in conjunction with medication delivery containers other than a pMDI container, including for example and without limitation nasal sprayers and powder inhalers.

As shown in FIGS. 1–3, the chamber housing 4, 20 defines an interior space 19 and further includes an output end 14, through which the medication is dispensed to the user. The length of the chamber housing 4, 20 as measured from point A to B as shown in FIGS. 1 and 3 is preferably between 70 mm and 160 mm in length and most preferably between 80 mm and 120 mm in length. The cross sectional area of the chamber housing 4, 20 is preferably between 700 mm2 and 7500 mm2 and most preferably between 700 mm2 and 2100 mm2. In a preferred embodiment, the chamber housing 4, 20 has a length of 120 mm and a cross sectional area of 19.6 cm2.

As shown in the embodiment of in FIGS. 1 and 2, the output end 14 includes a downstream portion 23 that is releasably secured to a main housing 21 with one or more fastening elements 25, 27. For example, the fastening elements can be configured as tabs and recesses in one preferred embodiment, which provides a snap-fit between the main housing 21 and the downstream portion 23.

In one preferred embodiment, shown in FIGS. 4–7, an adapter 30 includes an input end 32 configured as an insert portion that is fitted in an opening 27 formed in the output end 14 of the chamber housing. Conversely, the input end 32 can be fitted over or around an end portion of the chamber housing. The adapter further includes an output end 34 that, in one preferred embodiment, is shaped to be received in the mouth of the user. For example, the output end 34 can have an outer circular cross-section, or it can be elliptical, oval, obround or any other shaped suitable for insertion into the mouth of the user. Alternatively, an additional mouthpieces (not shown) can be fitted in or around the output end. In yet another alternative, a mask (not shown) can be fitted in or around the output end, wherein the mask is shaped to be disposed over the face, preferably including the mouth and nose, of the user. In yet another alternative embodiment, a nasal applicator, provided for example with prongs, can be fitted into or around the output end.

A middle portion 36 joins the input and output end. In one preferred embodiment, the middle portion 36 has an inner, central portion 40 that is tapered and follows the contour of an interior channel formed in the adapter. The shape of the middle portion, and in particular the central portion 40, provides indicia to the user about which end to secure to the holding chamber by indicating the flow direction. Additional indicia, besides the shape, such as arrows and words, can also be provided. Preferably, the middle portion includes a plurality of ribs 38 extending radially from the central portion 40 which join the input and output ends 32, 34.

Figure 6:
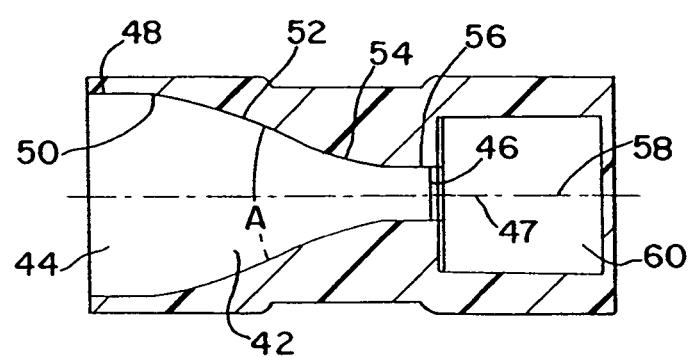
FIG. 6 is a cross-sectional view of the adapter taken along line 6—6 of FIG. 5.
Figure 7:
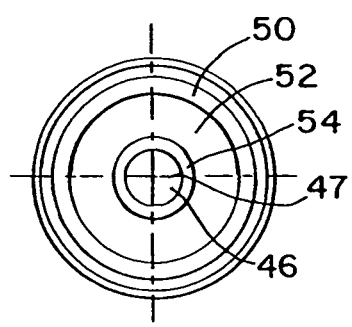
FIG. 7 is an end view of the adapter shown in FIG. 4.
Figure 8:
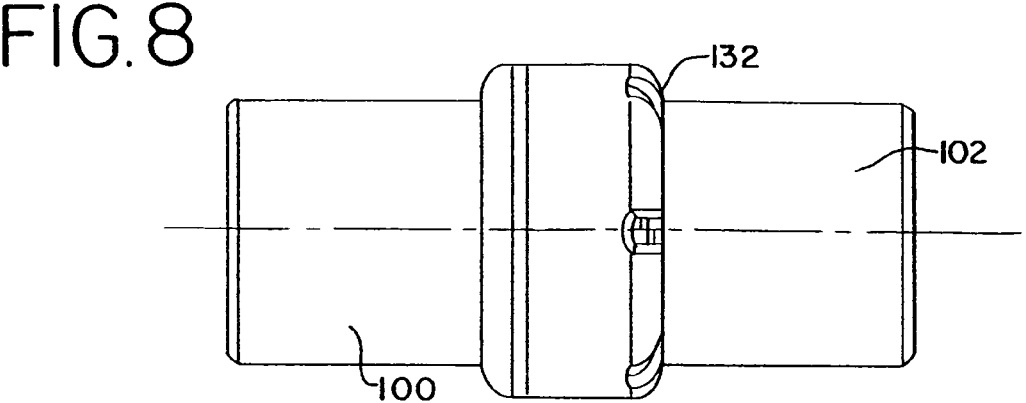
FIG. 8 is a side view of an alternative embodiment of an adapter.
Figure 9:
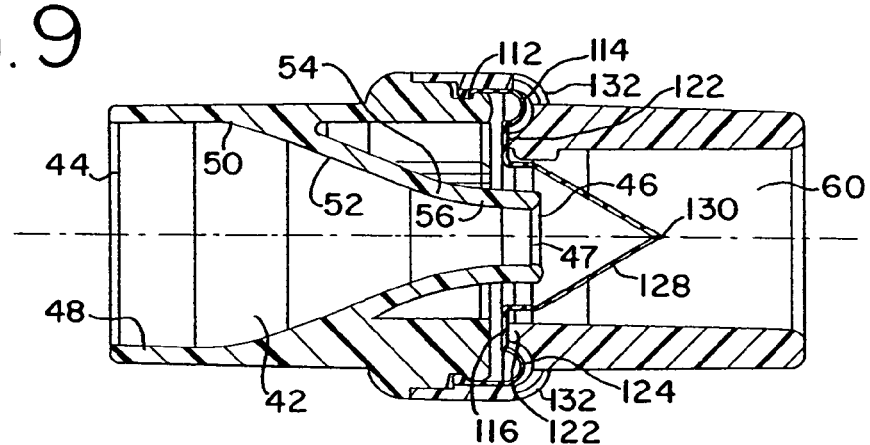
FIG. 9 is a cross-sectional view of the adapter shown in FIG. 8 during inhalation.
Figure 10:
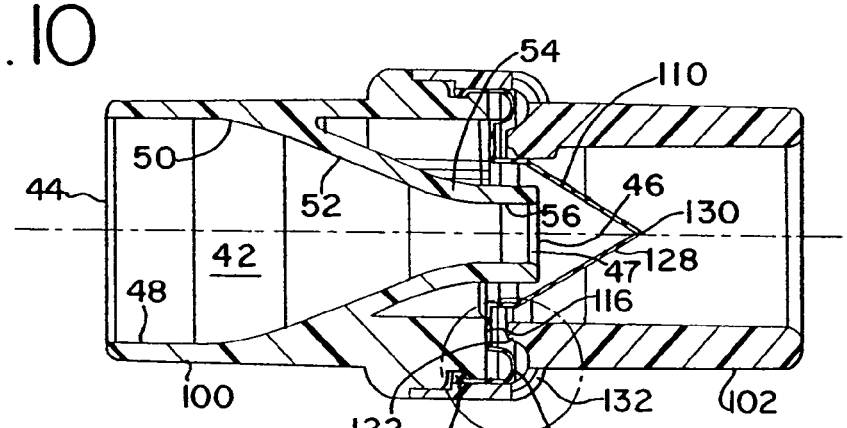
FIG. 10 is a cross-sectional view of the adapter shown in FIG. 8 during exhalation.
Figure 11:
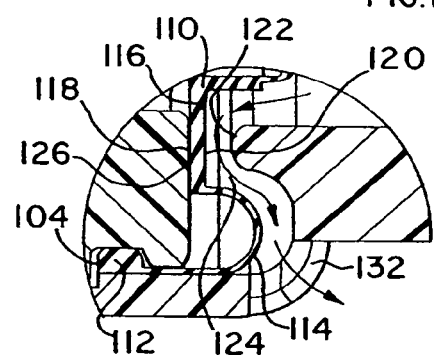
FIG. 11 is an enlarged, partial cross-sectional view taken along line 11 in FIG. 10.

Referring to FIGS. 6 and 7, the channel 42 has an upstream end 44 and a downstream end 46, which terminates in and defines an orifice 47. In one preferred embodiment, the channel 42 has a length of between about 20 mm and about 50 mm, more preferably a length of between about 25 mm and about 40 mm, and even more preferably a length of about 32 mm.

Preferably, the downstream end 46 has a cross-sectional area that is less than the cross-sectional area of the upstream end 44. Preferably, the channel 42 tapers between the upstream and downstream ends. Preferably the ratio of the cross-sectional area of the channel at the upstream end to the downstream end is between about 1.5:1 and about 6:1, and more preferably at a ratio of about 4:1.

For example, in one preferred embodiment, the upstream end 44 has a cross-sectional area of between about 200 mm$^2$ and about 350 mm$^2$, and more preferably about 283 mm$^2$, although greater and lesser areas may be suitable. In one preferred embodiment, the opening at the upstream end 44 is configured as a circular opening having a diameter between about 18 mm and about 20 mm, and more preferably a diameter of about 19 mm. Of course, other non-circular shapes and/or cross-sectional areas are acceptable.

Also in one exemplary preferred embodiment, the downstream end 46, and the orifice 47 formed at the end thereof, has a cross-sectional area of between about 3 mm$^2$ and about 201 mm$^2$, more preferably between about 7 mm$^2$ and about 78.5 mm$^2$, more preferably less than about 60 mm$^2$, even more preferably less than about 25 mm$^2$, and in one embodiment, preferably about 19.6 mm$^2$. In one preferred embodiment, the opening 47 at the downstream end 46 configured is a circular opening having a diameter between about 2 mm and about 16 mm, more preferably between about 3 mm and about 10 mm, more preferably less than about 7 mm, and more preferably about 5 mm. Of course, other non-circular shapes and/or cross-sectional areas are acceptable. Also, it should be understood that the channel may have a uniform cross-sectional area between the upstream and downstream end, preferably in the dimensions and ranges described above with respect to the downstream end.

In one preferred embodiment, an initial length 48 of the channel at the upstream end, for example about 4 mm, has a uniform cross-sectional area. Thereafter, the channel preferably tapers. For example, in one preferred embodiment, the channel includes a transitional region 50 having a concave shape, for example with a radius of about 20 mm, a frusto-conical portion 52, and a lower transitional region 54 having a convex shape, for example with a radius of about 20 mm. A final length 56 of the channel at the downstream end, for example about 2.92 mm, preferably again is configured with a uniform cross-sectional area. Preferably, the angle of the sidewalls of the conical portion is about 22° from the central axis 58, forming an angle A of about 44°. Of course, it should be understood that the curved transitional regions can be eliminated, or provided with different radii of curvature. Likewise, the lengths of the initial and final lengths of the channel can be omitted, and also the linear portion between the curved transition areas, such the entire cross-sectional area is tapered or changes along the length of the channel. Alternatively, the channel may be stepped down from a first cross-sectional area to a lesser second cross-sectional area, without any taper.

Referring to FIG. 6, the downstream end 46 of the channel 42, with its orifice 47, opens into an exhaust chamber 60 formed in the output end 34 of the adapter. Preferably, the exhaust chamber 60 has a length of about 16 mm, and a cross-sectional area of about 177 mm$^2$. In one preferred embodiment, the exhaust chamber 60 has a circular cross-section with an inner diameter of about 15 mm. In one preferred embodiment, an endotracheal (ET) tube having an outer diameter of about 15 mm is configured to fit therein.

Figure 12:
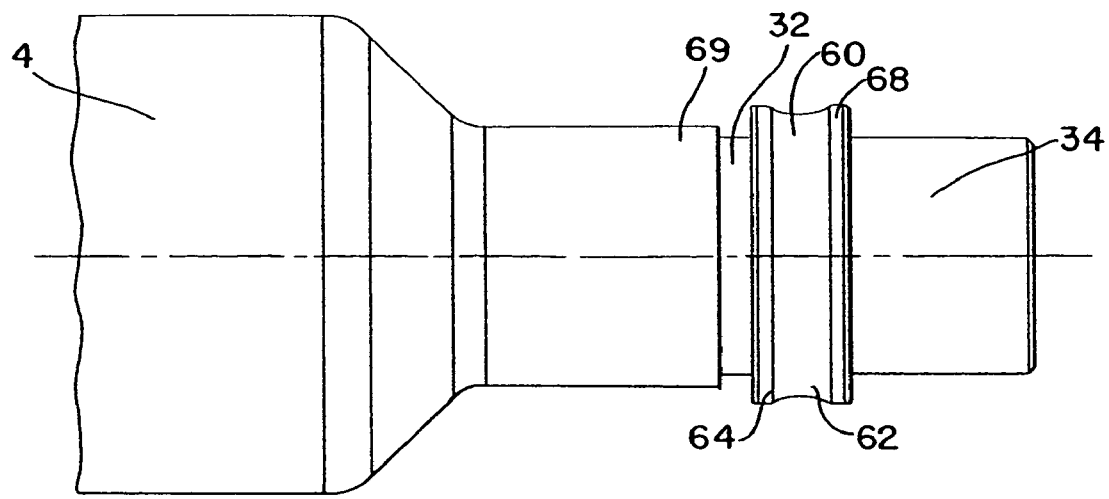
FIG. 12 is a partial side view of an alternative embodiment of an aerosol medication delivery system.
Figure 13:
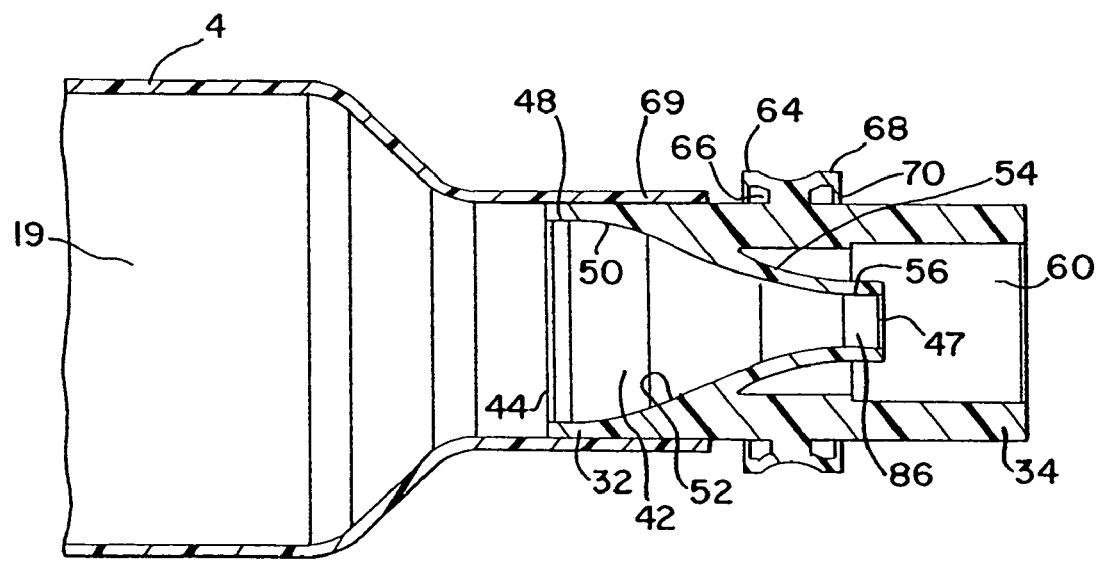
FIG. 13 is a partial cross-sectional view of the aerosol medication delivery system shown in FIG. 12 taken along line 13—13 of FIG. 12.

Referring to another preferred embodiment of the adapter, shown in FIGS. 12 and 13, the middle portion 90 is configured with a radially extending annular rib 62 positioned between the output and input ends. The rib 62 forms a shoulder 64 having a recess or annular channel 66 which receives an end 69 of the housing and limits the distance the adapter is inserted into the end of the chamber housing. A shoulder 68 also defines an outwardly facing annular channel 70 or recess that may receive the flange of a mouthpiece or mask as it is inserted onto or around the output end of the adapter. Referring to FIG. 13, the exhaust chamber 60 extends around the output end of the channel, to direct the aerosol into the center of the ET tube adapter or center of the mask connector.

In yet another preferred embodiment of the adapter, shown in FIGS. 8–11, the output and input ends are made as separate pieces 100, 102 that are secured one to the other in a snap-fit engagement, or by other devices such as a friction fit or locking device. In this embodiment, a valve 110, which serves both as an inhalation and exhalation valve, has an outer peripheral edge 112 configured with an enlarged portion or bead that is trapped and secured in a cavity 104 formed between the output and input pieces. The valve 110 includes a flexible U-shaped hinge portion 114 extending between the edge and a base portion 116 of the valve. The base portion has a first and second side 118, 120. The first side 120, which is directed toward the output piece, defines a sealing surface that mates with an annular rib portion 122 of the output piece. The rib portion 122 is spaced from an end surface 126 of the input piece to form an exhaust channel 124 therebetween, with the base portion 116 disposed therebetween in the exhaust channel 124. The valve 110 further includes a duckbill portion, having a pair of flat, flexible side walls 128, which extends upwardly from the periphery of a central opening formed in the base portion 116 and defines an apex 130. Preferably a slit is formed at the apex 130. The output piece 102 further includes a plurality of openings 132, or exhaust ports, that communicate with the exhaust chamber 60 of the adapter via the exhaust channel 124. Preferably, the valve 110 is circular, and includes an annular base portion 116, hinge portion 114 and edge portion 112.

It should be understood that the adapter could be molded as a one-piece unit with the valve being in-molded with the adapter, or inserted as a separate component. In addition, it should be understood that the valve can be configured in different shapes and can include a valve that has a central opening with a peripheral portion of the valve being seated on a valve seat, for example a baffle member secured in or adjacent to the channel. In such a configuration, the central portion moves away from the valve seat during inhalation, while an outer peripheral edge of the valve moves away from a valve seat formed on the output piece during exhalation. It should also be understood that the device can be configured with separate inhalation and exhalation valves.

It should be understood that the channel 42, with its downstream and upstream ends 46, 44 can be formed integrally in the output end of the chamber housing, for example by molding, without the need for an adapter. Likewise, the output end of the adapter, defining the mouthpiece, can be formed integrally as part of the chamber housing downstream of the channel. Alternatively, the output end of the adapter can be formed as a separate piece that is mounted to the chamber housing, having a channel, with a valve disposed therebetween as explained above with respect to FIGS. 8–11. As such, it should be understood that the term "output end" of the holding chamber includes the adapter when it is associated therewith. Likewise, it should be understood that the term "chamber housing" includes and incorporates the adapter when it is mounted thereto.

Preferably, the adapter 30 and the chamber housing 14 are made of a hard plastic, such as polypropylene. The valve member 110 is preferably made of a flexible material, including for example and without limitation a silicone, a thermoplastic elastomer, rubber, Ethylene-Propylene-Diene-Monomer (EPDM) or Berfluodelaastomers (FFKN).

In operation, the user actuates the dispenser 2, or other device, so as to discharge a medication, preferably in aerosol form, through the input end 6 into the interior space of the holding chamber 4, or chamber housing. The user thereafter inhales through the output end of the adapter 34, 102 and holding chamber. As the user inhales, the medicament, which is preferably in aerosol form, is drawn through the channel 42 from the upstream to the downstream ends 44, 46 thereof. The medicament is then expelled into the exhaust chamber 60 and through the user's mouth via an ET tube where it is deposited in their lungs.

In one preferred embodiment, which includes an inhalation and exhalation valve 110, the edges of the flat sidewalls 128 of the duck bill move away from each other at the slit formed at the apex 130 upon inhalation due to a pressure differential applied to the upstream side of the duckbill, so as to allow the medicament to move through the opening formed thereby. At the same time, the pressure is applied to the upstream side 118 of the base portion so as to seal the downstream side 120 against the valve seat formed by the rib portion 122.

Upon exhalation, a pressure is exerted on the downstream side of the sidewalls 128 causing the duck bill to close. The exhalation pressure, however, is also exerted on the downstream side 120 of the base portion 116, causing the base portion 116 to move away from the valve seat 122 as the hinge flexes 114. As the base portion 116 is unseated, the exhaust air from the user escapes through the channel 124 and openings 132 to the ambient environment. In this way, exhalation by the user does not force air, or any contaminants, back into the holding chamber 4.

The narrow orifice 47 formed in the output end 14, whether integrally or by way of an adapter, is ideally suited for administering medication to users or patients with low tidal volumes in the range of between about 5 ml to about 100 ml, and more preferably between about 5 ml and about 20 ml. The term "tidal volume" as used herein means the average volume inhaled and exhaled during periodic breathing, and generally needed to satisfy metabolic requirements. In particular, the narrow orifice 47, alone and in conjunction with the tapered channel 42, maximizes the emitted dose and respirable fraction of the aerosol. In particular, the velocity of the particles is increased and, is particularly concentrated along the axis or centerline of the channel 42. The increased velocity may increase the number of respirable particles from the population of larger particles, as well as help carry the particles through the system.

The holding chamber with its narrow orifice, whether integrally molded or formed in an adapter portion thereof, is suitable for both spontaneously breathing patients as well as those requiring assisted ventilation.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An aerosol medication delivery apparatus comprising: a holding chamber having an input end and an output end and defining an interior space, wherein said output end comprises an orifice having a cross-sectional area of less than about 60 mm$^2$, and wherein said output end comprises a channel having an upstream end and a downstream end, wherein said channel defines said orifice at said downstream end, wherein said channel comprises a tapered portion between said upstream end and said downstream end, and wherein said downstream and upstream ends have first and second cross-sectional areas respectively, wherein said first cross-sectional area of said downstream end is less than said second cross-sectional area of said upstream end.

2. The aerosol medication delivery apparatus of claim 1 wherein first said cross-sectional area is less than about 25 mm$^2$.

3. The aerosol medication delivery apparatus of claim 1 wherein said orifice has a circular cross-section.

4. The aerosol medication delivery apparatus of claim 3 wherein said orifice has a diameter of between about 2.0 and about 7.5 mm.

5. The aerosol medication delivery apparatus of claim 4 wherein said diameter is about 5 mm.

6. The aerosol medication delivery apparatus of claim 1 wherein said output end further comprises an inhalation valve disposed downstream of said orifice.

7. The aerosol medication delivery apparatus of claim 6 wherein said output end further comprises an exhalation valve.

8. The aerosol delivery apparatus of claim 1 wherein said tapered portion of said channel comprises a first transitional region having a concave shape and a second transitional region having a convex shape, wherein said second transitional region is positioned downstream of said first transitional region.

9. The aerosol delivery apparatus of claim 8 further comprising a frusto-conical portion disposed between said first and second transitional regions.

10. The aerosol delivery apparatus of claim 8 wherein said channel comprises a portion with a length having a uniform cross-section positioned upstream of said tapered portion.

11. The aerosol delivery apparatus of claim 10 wherein said length is about 4 mm.

12. The aerosol medication delivery apparatus of claim 1 wherein said output end of said holding chamber comprises an adapter configured with a user interface, said adapter defining said channel.

13. An aerosol medication delivery apparatus comprising:
a holding chamber having an input end and an output end and defining an interior space, wherein said output end comprises an orifice having a cross-sectional area of less than about 60 mm$^2$, wherein said holding chamber has a length of between 80 mm and 120 mm.

14. The aerosol medication delivery apparatus of claim 13 wherein said holding chamber has a cross sectional area of between 700 mm$^2$ and 2100 mm$^2$.

15. The aerosol medication delivery apparatus of claim 13 wherein said output end of said holding chamber comprises an adapter configured with a user interface, said adapter defining said orifice.

16. A method of administering an aerosol medication to a user comprising:
depositing a medication into a holding chamber through an input end of said holding chamber; and
drawing said medication through said holding chamber to an output end thereof;
drawing said medication into an upstream end of a channel communicating with said output end of said holding chamber, said upstream end defined by a first cross-sectional area;
funneling said medication through a tapered portion of said channel from said upstream end of said channel to an orifice positioned downstream from said upstream end of said channel, wherein said orifice has a second cross-sectional area of less than about 60 mm$^2$, and wherein said second cross-sectional area is less than said first cross-sectional area.

17. The method of claim 16 wherein said second cross-sectional area is less than about 25 mm$^2$.

18. The method of claim 16 wherein said orifice has a circular cross-section.

19. The method of claim 18 wherein said orifice has a diameter of between about 2.0 and about 7.5 mm.

20. The method of claim 19 wherein said diameter is about 5 mm.

21. The method of claim 16 further comprising inhaling and thereby drawing said medication through an inhalation valve positioned downstream of said orifice.

22. The method of claim 21 further comprising exhaling at least in part through an exhalation valve positioned downstream of said orifice.

23. The method of claim 16 wherein an adapter defines said orifice and said channel.

24. The method of claim 23 wherein said adapter comprises a mouthpiece, and further comprising inserting said mouthpiece into the mouth of a user and inhaling through said mouthpiece.

25. An aerosol medication delivery apparatus comprising:
a holding chamber having an input end and an output end and defining an interior space, said output end defining an opening;
an adapter having an input end coupled to said output end of said holding chamber and an output end, wherein said adapter comprises a channel extending from said input end of said adapter to said output end of said adapter, wherein said channel at said input end of said adapter comprises a first cross-sectional area, and wherein said channel defines an orifice downstream of said input end of said adapter, said orifice having a second cross-sectional area of less than about 60 mm$^2$, wherein said second cross-sectional area is less than said first cross-sectional area, and wherein said channel at said input end of said adapter is in fluid flow communication with said opening of said holding chamber output end with said orifice spaced from and positioned downstream of said opening.

26. The aerosol medication delivery apparatus of claim 25 wherein said output end of said adapter comprises a mouthpiece shaped to be inserted into the mouth of a user.

27. The aerosol medication delivery apparatus of claim 25 wherein said output end of said adapter comprises a mask shaped to be placed over the nose and mouth of a user.

28. The aerosol medication delivery apparatus of claim 25 further comprising a middle portion disposed between said input and output ends of said adapter, wherein said orifice is located in said middle portion, and wherein said middle portion has an exterior surface comprising directional indicia adapted to indicate the desired direction of medicament flow through the adapter.

29. The aerosol medication delivery apparatus of claim 28 wherein said input and output ends comprise respective exterior surfaces having substantially the same shape.

30. The aerosol medication delivery apparatus of claim 25 wherein said input end of said adapter is inserted inside said opening of said output end of said holding chamber.

31. The aerosol medication delivery apparatus of claim 30 wherein said adapter comprises an annular rib engaging the output end of said holding chamber.

32. The aerosol medication delivery apparatus of claim 31 wherein said annular rib comprises an annular channel shaped to receive said output end of said holding chamber.

33. The aerosol medication delivery apparatus of claim 25 wherein said adapter comprises an inhalation valve positioned downstream of said orifice and an exhalation valve.

* * * * *